(12) United States Patent
Bowe

(10) Patent No.: US 9,629,737 B2
(45) Date of Patent: Apr. 25, 2017

(54) DELIVERY SYSTEM FOR STAGED STENT RELEASE

(71) Applicant: Cook Medical Technologies LLC, Bloomington, IN (US)

(72) Inventor: Jason S. Bowe, Blaine, MN (US)

(73) Assignee: Cook Medical Technologies LLC, Bloomington, IN (US)

( * ) Notice: Subject to any disclaimer, the term of this patent is extended or adjusted under 35 U.S.C. 154(b) by 896 days.

(21) Appl. No.: 13/722,479

(22) Filed: Dec. 20, 2012

(65) Prior Publication Data

US 2013/0166012 A1 Jun. 27, 2013

Related U.S. Application Data

(60) Provisional application No. 61/579,962, filed on Dec. 23, 2011.

(51) Int. Cl.
*A61F 2/966* (2013.01)
*A61F 2/95* (2013.01)

(52) U.S. Cl.
CPC .............. *A61F 2/95* (2013.01); *A61F 2/966* (2013.01); *A61F 2002/9511* (2013.01); *A61F 2002/9517* (2013.01)

(58) Field of Classification Search
CPC .............. A61F 2002/9511; A61F 2/95; A61F 2002/9665; A61F 2/962; A61F 2/966; A61F 2002/9517
See application file for complete search history.

(56) References Cited

U.S. PATENT DOCUMENTS

| | | |
|---|---|---|
| 5,776,142 A | 7/1998 | Gunderson |
| 6,352,561 B1 | 3/2002 | Leopold et al. |
| 6,371,979 B1 | 4/2002 | Beyar et al. |
| 6,761,733 B2 | 7/2004 | Chobotov et al. |
| 7,393,357 B2 | 7/2008 | Stelter et al. |
| 7,780,717 B2 | 8/2010 | Ducke et al. |
| 2003/0225446 A1 | 12/2003 | Hartley |

(Continued)

OTHER PUBLICATIONS

Extended European Search Report, European Patent Application 12199010.5, dated Jun. 12, 2013, pp. 1-7, European Patent Office, Munich, Germany.

*Primary Examiner* — Katherine M Shi
*Assistant Examiner* — Michael Mendoza
(74) *Attorney, Agent, or Firm* — Brinks Gilson & Lione

(57) ABSTRACT

A prosthesis introducer system may include an introducer. A trigger wire release mechanism and a restraining member may be positioned near the distal end of the introducer. The system may include first and second trigger wires, each including a proximal portion releasably coupleable to a portion of a prosthesis and a distal portion coupled to the trigger wire release mechanism. The second trigger wire may be engaged by the restraining member. Each of the first and second trigger wires may include a taut portion. The second trigger wire may include a slack portion extending distally from the taut portion and positioned distal of the restraining member. Upon actuation of the trigger wire release mechanism, the first trigger wire may be releasable from the prosthesis and the second trigger wire may be releasable subsequent to the release of the first trigger wire.

17 Claims, 6 Drawing Sheets

(56) References Cited

U.S. PATENT DOCUMENTS

| | | | |
|---|---|---|---|
| 2004/0260383 A1* | 12/2004 | Stelter | A61F 2/07 623/1.11 |
| 2006/0004433 A1 | 1/2006 | Greenberg et al. | |
| 2007/0219614 A1 | 9/2007 | Hartley | |
| 2007/0260301 A1 | 11/2007 | Chuter et al. | |
| 2009/0192585 A1 | 7/2009 | Bloom et al. | |
| 2009/0204202 A1 | 8/2009 | Dierking et al. | |
| 2009/0270971 A1 | 10/2009 | Xiao et al. | |
| 2010/0161027 A1 | 6/2010 | Orr | |
| 2010/0168756 A1 | 7/2010 | Dorn et al. | |
| 2010/0174354 A1 | 7/2010 | Hyodoh et al. | |
| 2010/0274187 A1 | 10/2010 | Argentine | |
| 2011/0054585 A1 | 3/2011 | Osborne | |

\* cited by examiner

DELIVERY SYSTEM FOR STAGED STENT RELEASE

CROSS-REFERENCE TO RELATED APPLICATIONS

This application claims priority and the benefit of provisional U.S. Patent Application Ser. No. 61/579,962, filed Dec. 23, 2011, which is incorporated herein by reference in its entirety.

TECHNICAL FIELD

This disclosure relates to medical devices and more particularly to an introducer and a means for retaining and releasing an expandable, intraluminal prosthesis for the endovascular repair of diseased or damaged vessels.

BACKGROUND

The embodiments described in this disclosure will generally be discussed in relation to deployment of stent grafts into the aorta, but this disclosure is not so limited and can be applied to other vasculature or other body lumens.

Prostheses such as stents or stent grafts may be inserted into an anatomical vessel or duct for various purposes. Stents may maintain or restore patency in a formerly blocked or constricted passageway, for example, following a balloon angioplasty procedure. Other stents may be used for different procedures. For example, stents placed in or about a graft have been used to hold the graft in an open configuration to treat an aneurysm. Additionally, stents coupled to one or both ends of a graft may extend proximally or distally away from the graft to engage a healthy portion of a vessel wall away from a diseased portion of an aneurysm to provide endovascular graft fixation.

Stents may be either self-expanding or balloon-expandable. Stents also can have characteristics of both self-expanding and balloon-expandable stents. Self-expanding stents may be delivered to a target site in a compressed configuration and subsequently expanded by removing a delivery sheath, removing trigger wires, and/or releasing diameter reducing ties. A self-expanding stent may expand primarily based on its own expansive force without the need for further mechanical expansion. A stent may be made of a shape-memory alloy such as nitinol to cause the stent to return to a predetermined configuration upon removal of the sheath or other device maintaining the stent in its predeployment compressed configuration.

When trigger wires are used as a deployment control mechanism, the trigger wires may releasably couple the proximal and/or distal ends of a stent or stent graft to a delivery catheter. Typically, one or more trigger wires are looped through a portion of the stent near a vertex of the stent. For example, trigger wires may be used to restrain a "Z-stent" or Gianturco stent comprising a series of substantially straight segments interconnected by a series of bent segments. The trigger wires may be disposed through, and pull upon, the bent segments to pull the stent closely against the delivery catheter.

Trigger wires also may be used in conjunction with different stent designs such as cannula-cut stents having relatively acute or pointed bends. The designs of cannula-cut stents may facilitate compression of the stent to a relatively small delivery profile due to the tight bends of the apices. With such stents, the trigger wires may be looped around one or more vertices corresponding to the proximal and/or distal apices, e.g., a location where an individual apex splits into two separate strut segments.

Releasing the trigger wires will release the stent from the delivery catheter to allow the stent to expand. Multiple trigger wires generally may be released simultaneously. Depending, for example, on the number of trigger wires and the radial expansion force exerted by the stent, releasing the trigger wires may require a relatively great amount of force. Additionally, upon releasing the trigger wires, the stent may expand relatively quickly causing undesirable movement of the stent within a vessel.

In view of the above, it would be desirable to provide a delivery system requiring a reduced amount of force for releasing the trigger wires. It would also be desirable to provide a delivery system capable of releasing a stent in stages to better control the placement of the stent within a vessel.

SUMMARY

The present embodiments provide a delivery system for intraluminal deployment of a stent.

In one example, a prosthesis introducer system may include an introducer having a proximal end and a distal end. At least one trigger wire lumen may extend at least partly between the proximal end and the distal end of the introducer. A trigger wire release mechanism may be positioned near the distal end of the introducer. A restraining member may be positioned near the distal end of the introducer. The system may include a first trigger wire and a second trigger wire extending through the at least one trigger wire lumen. Each of the first trigger wire and the second trigger wire may include a proximal portion releasably coupleable to a portion of a prosthesis and a distal portion coupled to the trigger wire release mechanism. At least the second trigger wire may be engaged by the restraining member. Each of the first trigger wire and the second trigger wire may include a taut portion. At least the second trigger wire may include a slack portion extending distally from the taut portion and positioned distal of the restraining member. Upon actuation of the trigger wire release mechanism, the first trigger wire may be releasable from the prosthesis and then the second trigger wire may be releasable from the prosthesis subsequent to the release of the first trigger wire.

In another example, a prosthesis introducer system may include an introducer including an inner cannula and an outer cannula. The inner cannula may have a proximal end, a distal end, and a lumen extending between the proximal end and the distal end of the inner cannula. The outer cannula may have a proximal end, a distal end, and a lumen extending between the proximal end and the distal end of the outer cannula. The inner cannula may be at least partially received within the lumen of the outer cannula. The introducer may include a trigger wire release mechanism positioned near the distal end of the outer cannula and a restraining member positioned near the distal end of the outer cannula. The system may include an expandable endoluminal prosthesis positioned on the inner cannula. The system may include a first trigger wire and a second trigger wire extending through an annular space between the inner cannula and the outer cannula. Each of the first trigger wire and the second trigger wire may have a proximal portion releasably coupled to a portion of the prosthesis and a distal portion coupled to the trigger wire release mechanism. Each of the first trigger wire and the second trigger wire may be engaged by the restraining member. Each of the first trigger wire and the second trigger wire may have a taut portion and a slack portion extending distally from the taut portion and positioned distal of the restraining member. The slack portion of the second trigger wire may be longer than the slack portion of the first trigger wire. Upon actuation of the trigger wire release mechanism, the first trigger wire may be released from the prosthesis and then the second trigger wire may be released from the prosthesis subsequent to the release of the first trigger wire.

In yet another example, a method of deploying a prosthesis within a body vessel may include introducing the prosthesis into the body vessel on an introducer. The introducer may include a trigger wire release mechanism positioned near a distal end of the introducer and a restraining member positioned near the distal end of the introducer. The introducer may include a first trigger wire and a second trigger wire. Each of the first trigger wire and the second trigger wire may have a proximal portion releasably coupled to a portion of the prosthesis and a distal portion coupled to the trigger wire release mechanism. Each of the first trigger wire and the second trigger wire may be engaged by the restraining member and may include a slack portion positioned distal of the restraining member. The slack portion of the second trigger wire may be longer than the slack portion of the first trigger wire. The method may include partially expanding the portion of the prosthesis by releasing the first trigger wire from the prosthesis by retracting the trigger wire release mechanism a first distance relative to the prosthesis. The method may include further expanding the portion of the prosthesis by releasing the second trigger wire from the prosthesis by retracting the trigger wire release mechanism a second distance relative to the prosthesis.

Other systems, methods, features, and advantages of the invention will be, or will become, apparent to one with skill in the art upon examination of the following figures and detailed description. It is intended that all such additional systems, methods, features, and advantages be within the scope of the invention, and be encompassed by the following claims.

BRIEF DESCRIPTIONS OF THE DRAWINGS

DETAILED DESCRIPTION OF THE DRAWINGS AND THE PRESENTLY PREFERRED EMBODIMENTS

The present disclosure relates to a delivery system for intraluminal deployment of a stent graft.

In the present disclosure, the term "proximal" refers to a direction that is generally closest to the heart during a medical procedure, while the term "distal" refers to a direction that is farthest from the heart during a medical procedure.

The term "stent graft" refers to a device which has a tubular body of biocompatible graft material and at least one stent fastened to the tubular body to define a lumen through the stent graft. The stent graft may be bifurcated and/or may have fenestrations, side arms, or the like. Other arrangements of stent grafts also are within the scope of this disclosure.

Figure 1:
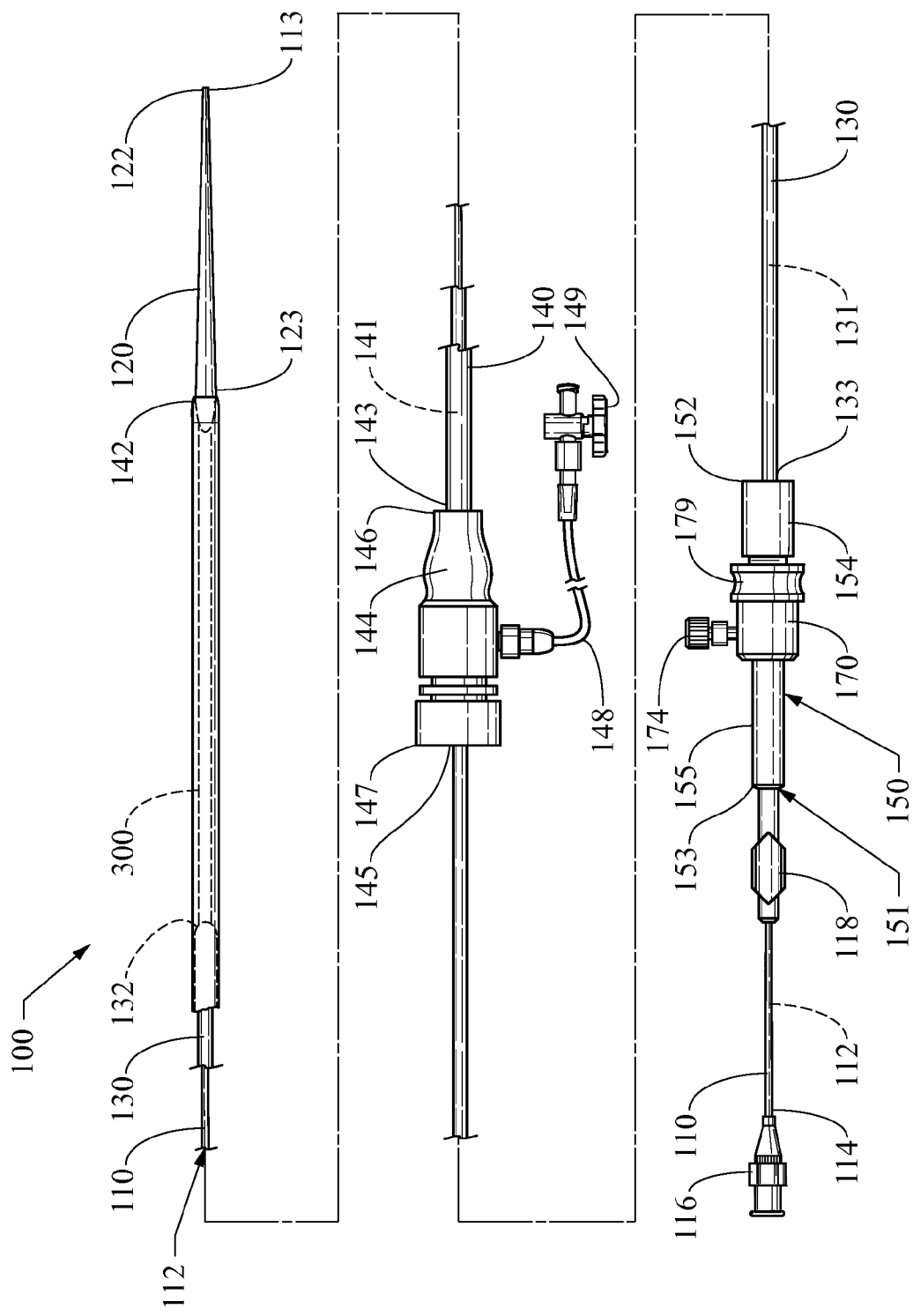
FIG. 1 depicts one example of an introducer system.
Figure 2:
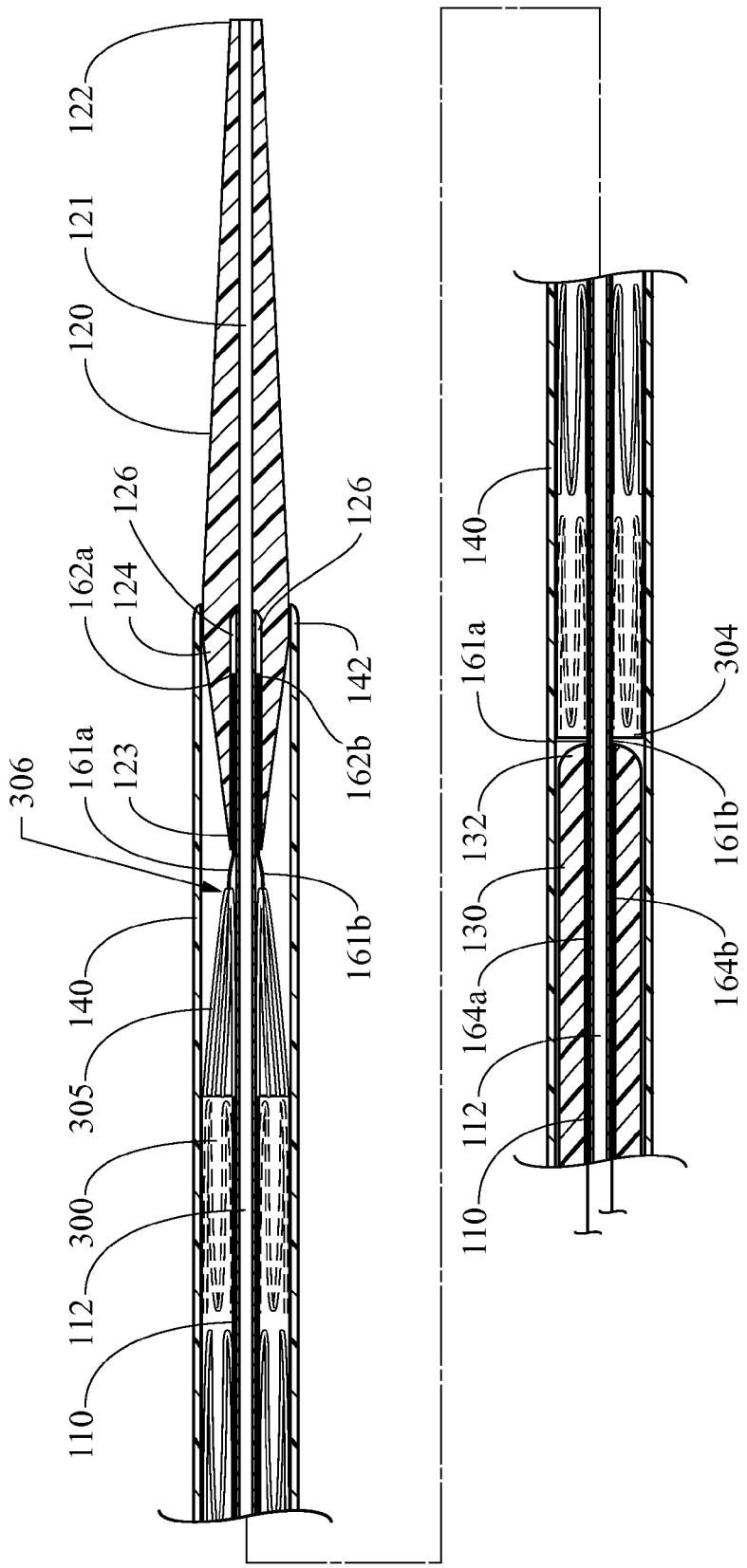
FIG. 2 is a partial longitudinal cross sectional view of a proximal portion of the introducer system of FIG. 1.

FIG. 1 depicts one embodiment of an introducer 100, and FIG. 2 depicts a longitudinal cross sectional view of a proximal portion of the introducer. The introducer 100 may include an inner cannula 110. The inner cannula 110 may be configured as an elongate tubular member having a generally cylindrical shape. A lumen 112 may extend generally longitudinally within the inner cannula 110 between a proximal end 113 and a distal end 114 thereof. The lumen 112 may be configured to receive a guide wire (not shown) to aid in navigating the introducer 110 to a desired location within the vasculature of a patient. The inner cannula 110 may be sufficiently flexible to enable the introducer 100 to be advanced within a relatively tortuous vessel such as the femoral artery. The inner cannula 110 may be attached to a distal manipulation portion such as a handle as further described below. A distal connector 116 (e.g., a Luer lock connector or any other suitable connector known in the art) may be attached to the distal end 114 of the inner cannula 110. The distal connector may enable the introduction of a fluid into the lumen 112 of the inner cannula 110 in a conventional manner. The proximal end 113 of the inner cannula 110 may be attached to a tip such as a nose cone 120.

The nose cone 120 may be configured to serve as a dilator for the introducer 100. To that end, the nose cone 120 may include a long, tapered, flexible extension having a generally conical shape. The tapered shape and flexibility of the extension may aid in advancing the introducer 100 within a body vessel of the patient. A proximal end 122 of the nose cone 120 may have a rounded, chamfered, or otherwise atraumatic shape to minimize trauma to a body vessel during introduction and navigation of the introducer 100 within the patient's body. Such an atraumatic tip may minimize pain and/or discomfort to the patient during introduction and navigation of the introducer 100 within the patient's body. A lumen 121 may extend generally longitudinally within the nose cone 120 between the proximal end 122 and a distal end 123 thereof. The inner cannula 110 may be attached to the distal end 123 of the nose cone 120. Alternatively, the inner cannula 110 may be received within the lumen 121 of the nose cone 120. In this configuration, the proximal end 113 of the inner cannula 110 may terminate distal to the proximal end 122 of the nose cone 120, or the proximal end of the inner cannula and the proximal end of the nose cone may be substantially coterminous.

The introducer 100 may include an outer cannula 130. The outer cannula 130 may be configured as an elongate tubular member having a generally cylindrical shape. The outer cannula 130 may be sufficiently flexible to enable the introducer 100 to be advanced within a relatively tortuous vessel such as the femoral artery. A lumen 131 may extend generally longitudinally within the outer cannula 130 between a proximal end 132 and a distal end 133 thereof. The lumen 131 may be configured to receive the inner cannula 110. In one example, the inner cannula 110 may be received within the outer cannula 130 such that the inner cannula and the outer cannula may be substantially coaxial. An annular space may be formed between the inner cannula 110 and the outer cannula 130 as further described below. The inner cannula 110 may move (e.g., by translation and/or rotation) relative to the outer cannula 130 or vice versa. A pin vise 118 may be positioned near the distal end 114 of the inner cannula 110 to lock the position of the inner cannula relative to the outer cannula 130. The distal end 133 of the outer cannula 130 may be attached to the handle of the introducer 100 as further described below. The proximal end 132 of the outer cannula 130 may be positioned near the distal end of a prosthesis also as further described below.

A sheath 140 may be positioned surrounding at least a portion of the inner cannula 110 and the outer cannula 130. The sheath 140 may be configured as an elongate tubular member having a generally cylindrical shape. The sheath 140 may be sufficiently flexible to enable the introducer 100 to be advanced within a relatively tortuous vessel such as the femoral artery. A lumen 141 may extend generally longitudinally within the sheath 140 between a proximal end 142 and a distal end 143 thereof. The inner cannula 110 and the outer cannula 130 may be received within the sheath 140 such that the inner cannula, the outer cannula, and the sheath may be substantially coaxial. The sheath 140 may move (e.g., by translation and/or rotation) relative to the inner cannula 110 and/or the outer cannula 130. To that end, a sheath termination hub 144 may be attached to the distal end 143 of the sheath 140. The sheath termination hub may be configured as a generally tubular member having a lumen 145 extending longitudinally between a proximal end 146 and a distal end 147 thereof. The sheath 140 may extend entirely through the lumen 145 of the sheath termination hub 144 to the distal end 147 thereof. Alternatively, the distal end 143 of the sheath 140 may terminate near the distal end 147 of the sheath termination hub 144. The inner cannula 110 and the outer cannula 130 may be received within the lumen 145 of the sheath termination hub 144 as shown in FIG. 1. The sheath termination hub 144 may translate longitudinally relative to the inner cannula 110 and/or the outer cannula 130 to cause the sheath 140 to translate as further described below. The sheath termination hub may include a side tube 148 having a connector 149 such as a Luer lock connector or any other suitable connector known in the art.

The introducer 100 also may include a distal manipulation portion. The distal manipulation portion may be configured as a handle 150 as shown in FIG. 1. The handle 150 may be configured as a generally tubular member having a lumen 151 extending longitudinally therethrough between a proximal end 152 and a distal end 153 thereof. The handle 150 may include a proximal portion 154 and a distal portion 155. Each of the proximal and distal portions 154, 155 may be configured as a tubular member having a substantially cylindrical shape. The proximal portion 154 may have a greater diameter than the distal portion 155 as shown in FIG. 1. The handle 150 may be fixedly attached to the distal end 133 of the outer cannula 130. The lumen 151 of the handle may be in communication with the lumen 131 of the outer cannula 130. The inner cannula 110 may be received within the lumen 151 of the handle 150. The handle 150 may be movable relative to the inner cannula 110 to cause a corresponding movement of the outer cannula 130 relative to the inner cannula.

The introducer 100 may have any other configuration suitable for use with the trigger wire system described below. For example, the introducer 100 may be configured as described in U.S. Pat. No. 7,393,357 to Stelter et al. or in U.S. Patent Application Pub. Nos. 2003/0225446 by Hartley; 2006/0004433 by Greenberg et al.; or 2007/0260301 by Chuter et al., which are incorporated herein by reference in their entirety.

Figure 3:
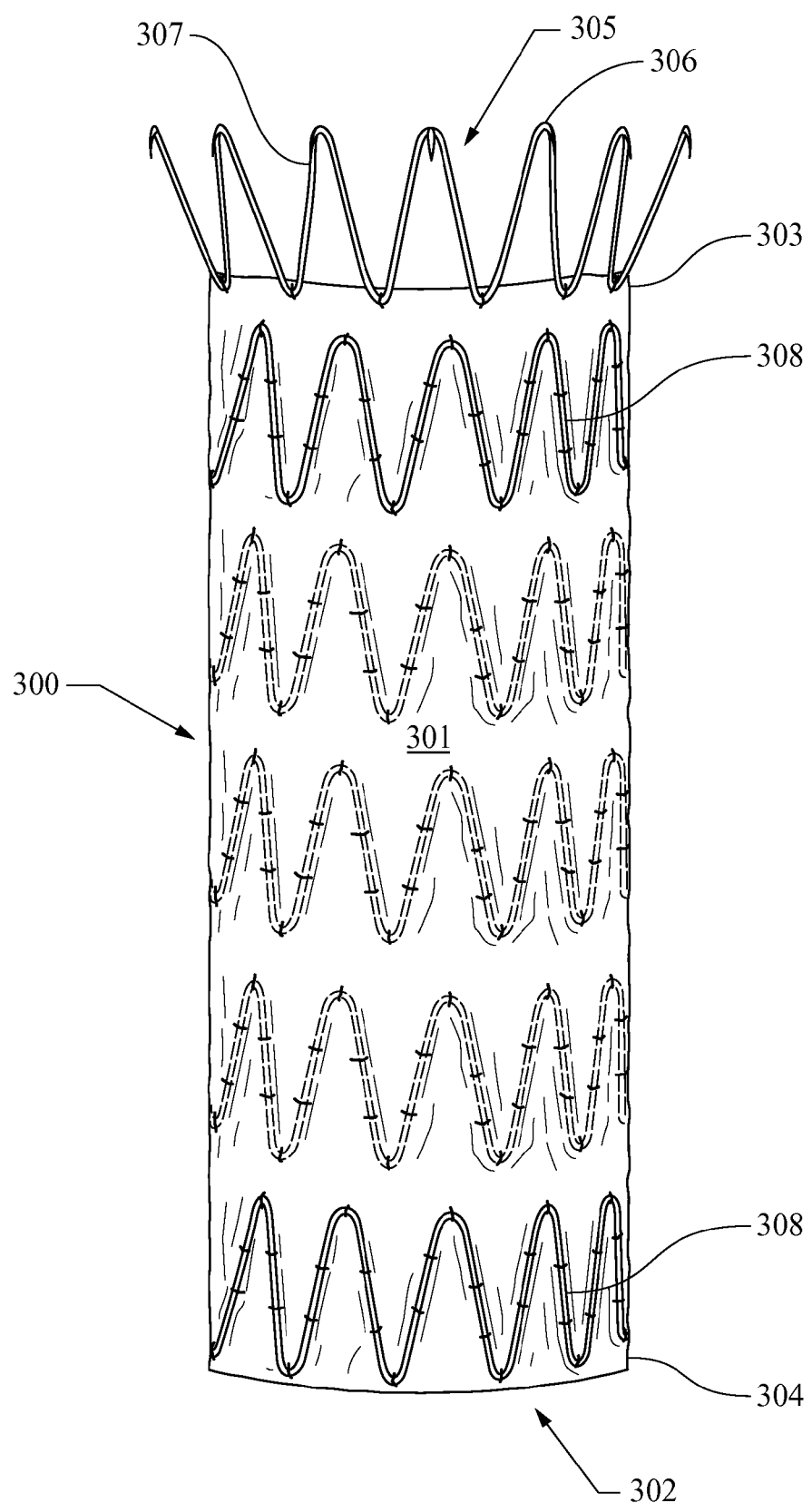
FIG. 3 depicts one example of a stent graft.

A prosthesis may be loaded into the introducer 100 for delivery within a patient's body. In one example, the prosthesis may be a stent graft. FIG. 3 depicts one embodiment of a stent graft 300 that may be deployed using the introducer 100. The stent graft 300 may be of a self expanding type having resilient stents to enable the stent graft to expand upon release from the introducer 100. The stent graft 300 may include a graft body 301 having a generally tubular configuration. The graft body 301 may have a lumen 302 extending longitudinally between a proximal end 303 and a distal end 304 thereof. A first zigzag stent 305 may extend beyond the proximal end 303 of the graft body 301. An end of the stent 305 may form a proximal end 306 of the stent graft. For example, the proximal end 306 may be defined by a plurality of bends of the stent 305. The stent 305 may include distally extending projections 307. The projections 307 may be configured as barbs as shown in FIG. 3. Such barbs may be configured to engage a wall of a body vessel upon deployment of the stent graft from the introducer to fix the stent graft in place relative to the body vessel. Additional stents 308 may be positioned along the length of the graft body 301.

Although the operation of the introducer 100 will be described with reference to the stent graft 300, a person having ordinary skill in the art will recognize that the introducer may be used with a stent or stent graft having any other configuration. For example, the introducer 100 may be used for intraluminal deployment of bifurcated stent grafts, stent grafts having branches, scallops, and/or fenestrations, or any other type of stent graft. The introducer 100 also may be used for intraluminal deployment of bare stents or any other type of prosthesis including a self expanding stent. Such modifications are contemplated by and within the scope of this disclosure.

The stent graft 300 may be loaded into the introducer 100 as shown in FIGS. 1-2. The stent graft 300 may be positioned around the inner cannula 110 such that the inner cannula extends longitudinally within the lumen 302 of the stent graft. The stent graft 300 may be compressed into a reduced diameter delivery configuration as is well known in the art. The sheath 140 may extend proximally from the sheath termination hub 144 such that the proximal end 142 of the sheath may engage the nose cone 120. To that end, the distal end 123 of the nose cone 120 may be received within the lumen 141 of the sheath as shown in FIG. 2. The stent graft 300 may be received within the lumen 141 of the sheath to retain the stent graft in the delivery configuration. In other words, the sheath 140 may oppose the radial expansive force of the stent graft 300 to retain the stent graft in the reduced diameter delivery configuration.

The distal end 304 of the stent graft 300 may be positioned near and proximal to the proximal end 132 of the outer cannula 130. In one example, the proximal end 132 of the outer cannula 130 may be in abutting contact with the distal end 304 of the stent graft 300. The proximal end 306 of the stent graft 300 may be positioned near and distal to the distal end 123 of the nose cone 120. As shown in FIG. 2, the nose cone 120 may have a tapered distal portion 124. The tapered distal portion 124 may aid in advancing the sheath 140 over the distal end 123 of the nose cone 120 to engage the nose cone as described above. The tapered distal portion 124 may taper in a distal direction from a diameter substantially equal to the diameter of the lumen 141 of the sheath 140 to a diameter substantially equal to the diameter of the inner cannula 110. The taper may be generally smooth and continuous as shown in FIG. 2. Alternatively, the distal end 123 of the nose cone 120 may terminate in a blunt surface.

Figure 4:
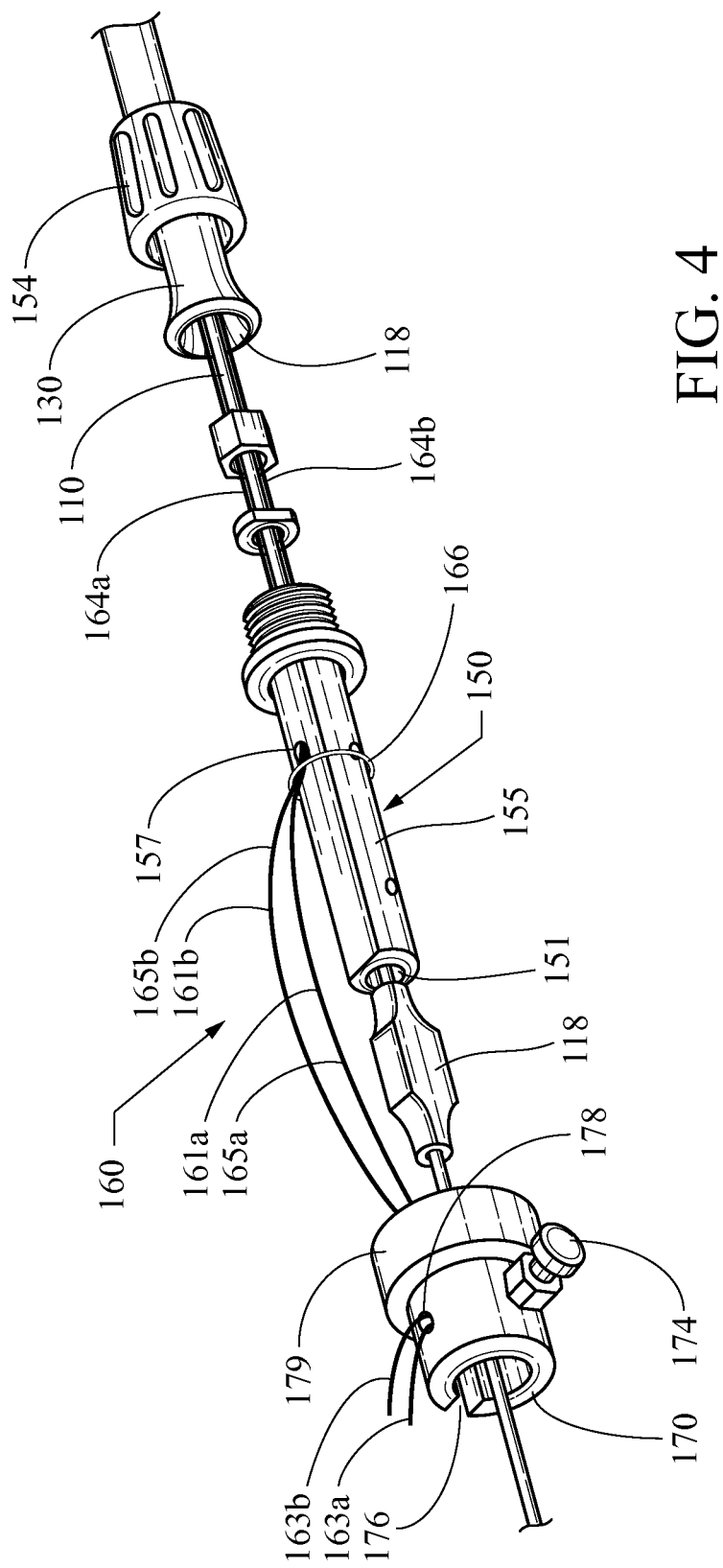
FIG. 4 is a partial perspective view of the distal manipulation portion of the introducer system of FIG. 1.

FIG. 4 is a partially exploded perspective view of a distal portion of the introducer 100 including a trigger wire system 160 and a trigger wire release mechanism 170. The introducer system 100 may include the trigger wire system 160 to retain at least a portion of the stent graft 300 in a compressed configuration as shown in FIG. 2. The trigger wire system 160 may include a plurality of trigger wires 161. Each of the plurality of trigger wires 161 may be configured as a flexible filamentary member having a proximal end and a distal end. For example, the trigger wire system 160 may include a first trigger wire 161a and a second trigger wire 161b as shown in FIGS. 2 and 4. For clarity, much of the following discussion will refer to a trigger wire system having two trigger wires. However, it will be apparent to one of ordinary skill in the art that any number of trigger wires may be used. Therefore, embodiments having any number of trigger wires are contemplated by and within the scope of this disclosure. The trigger wires may be formed from any suitable material and may have any suitable size. In one example, the trigger wires may be formed from nitinol wire having a diameter of about 0.010 in.

The first trigger wire 161a may have a proximal end 162a and a distal end 163a. Likewise, the second trigger wire may have a proximal end 162b and a distal end 163b. The distal ends 163a, 163b of the first and second trigger wires 161a, 161b may be attached to the trigger wire release mechanism 170 as shown in FIG. 4. The trigger wire release mechanism 170 may be configured as a substantially tubular member having a lumen extending therethrough. The trigger wire release mechanism 170 may be movable from a delivery configuration to a release configuration. FIG. 1 shows the trigger wire release mechanism 170 in the delivery configuration. In the delivery configuration, the trigger wire release mechanism 170 may be positioned around the distal portion 155 of the handle 150. In other words, the handle 150 may extend within the lumen of the trigger wire release mechanism 170. A retaining member 174 (shown in FIG. 4) may be configured to fix the trigger wire release mechanism in place relative to the handle 150. The retaining member 174 may be configured as a conventional thumbscrew. Alternatively, the retaining member 174 may have any other configuration known in the art (e.g., a push button or a pin vise). The retaining member 174 may be released and the trigger wire release mechanism 170 may be moved distally along the handle 150 to the release configuration shown in FIG. 4. In the release configuration, the trigger wire release mechanism 170 may be positioned surrounding the inner cannula 110 and distal to the handle 150. A slot 176 may be formed through a sidewall of the trigger wire release mechanism 170. The slot 176 may extend along substantially an entire length of the trigger wire release mechanism 170. The inner cannula 110 may be passed through the slot 176 to remove the trigger wire release mechanism 170 from the inner cannula. The trigger wire release mechanism 170 may be removed from the inner cannula 110 following (or during) deployment of the stent graft 300, as further described below, to reduce the potential for entangling the trigger wire release mechanism or the trigger wires with other components of the introducer or other medical instruments.

The distal ends 163a, 163b of the first and second trigger wires 161a, 161b may be attached to the trigger wire release mechanism 170 by any means. For example, the first and second trigger wires 161a, 161b may extend through and be engaged by an opening 178 formed in the sidewall of the trigger wire release mechanism 170 as shown in FIG. 4. The first and second trigger wires 161a, 161b may extend proximally within the lumen of the trigger wire release mechanism 170 and through an opening 157 formed in the handle 150. The opening 157 may be in communication with the lumen 151 of the handle 150 and/or the lumen 131 of the outer cannula 130. The first and second trigger wires 161a, 161b may further extend into an annular space 118 formed between the inner cannula 110 and the outer cannula 130.

An intermediate portion of each trigger wire 161 may be releasably coupled to the handle 150. To that end, the trigger wire system 160 may include a restraining member 166. The restraining member 166 may releasably couple the trigger wires 161 to the handle 150. In one example, the restraining member 166 may be configured as a ring member positioned around the distal portion 155 of the handle 150 as shown in FIG. 4. The ring member may at least partially circumscribe the distal portion 155 of the handle 150. The ring member may be configured as an elastic ring such as, for example, an o-ring, spring, or rubber band. Alternatively, the ring may be configured as a non-elastic ring such as a suture, wire, or string. The first and second trigger wires 161a, 161b may be slidably received between the ring and the distal portion 155 of the handle 150. The ring may exert a sufficient inward radial force to retain the intermediate portions of the trigger wires in place relative to the handle 150 to form slack portions in the trigger wires as further described below. The first and second trigger wires 161a, 161b may slide between the ring and the handle 150 upon application of a sufficient force, such as by moving the trigger wire release mechanism from the delivery position to the release position. In another example, the opening 157 of the handle 150 may be configured as the restraining member 166. The opening 157 may releasably engage the first and second trigger wires 161a, 161b passing therethrough to releasably couple the intermediate portions of the trigger wires to the handle 150. The releasable engagement may be in the form of frictional engagement. In other words, the opening 157 may be sized such that a frictional force between the trigger wires and the opening may be sufficient to fix the positions of the intermediate portions of the trigger wires 161 relative to the handle 150. Additionally, or alternatively, the opening 157 may be partially or completely filled with an elastic material which may exert a frictional force on the trigger wires 161 (e.g., by squeezing the trigger wires). The elastic material may be configured, for example, as a valve gasket. The first and second trigger wires 161a, 161b may slide within the opening 157 upon application of a sufficient force, such as by moving the trigger wire release mechanism from the delivery position to the release position.

The intermediate portions of the trigger wires 161 may be releasably coupled to the handle 150 by any means such as, for example, staples or adhesives. The plurality of trigger wires 161 may be coupled to the handle 150 together, such as by a single restraining member 166. Alternatively, each trigger wire 161 may be coupled to the handle individually, such as by multiple restraining members 166 or by adhesive applied to each trigger wire.

The first and second trigger wires 161a, 161b may extend proximally within the annular space 118 between the inner cannula 110 and the outer cannula 130 as shown in FIG. 4. In this manner, the annular space 118 may be configured as a trigger wire lumen. The first and second trigger wires 161a, 161b may exit the proximal end 132 of the outer cannula 130 and extend proximally within the lumen 302 of the stent graft 300 as shown in FIG. 2. The first and second trigger wires 161a, 161b may engage the proximal end 306 of the stent graft 300 to retain the proximal end of the stent graft in a compressed configuration as further described below. For example, the first trigger wire 161a may pass between adjacent struts of the stent 305 to engage a bend formed therebetween. In other words, the first trigger wire 161a may pass through the stent 305 to at least partially surround a bend at the proximal end 306 thereof. The second trigger wire 161b may engage the proximal end 306 of the stent graft 300 in a similar manner. Preferably, the second trigger wire 161b may engage a different bend of the stent 305 than the bend engaged by the first trigger wire 161a, such as a bend positioned opposite the bend engaged by the first trigger wire 161a relative to a circumference of the stent graft 300 as shown in FIG. 2.

The proximal ends 162a, 162b of the first and second trigger wires 161a, 161b may be releasably coupled to the nose cone 120 by any means. For example, the proximal ends 162a, 162b of the first and second trigger wires 161a, 161b may be received in at least one trigger wire port 126 formed in the nose cone 120. The trigger wire port 126 of the nose cone may be configured to frictionally engage the trigger wires such that pulling the trigger wires distally with sufficient force may release the wires from the nose cone. Additionally, or alternatively, the trigger wires 161 may be releasably coupled to the nose cone by any suitable means such as, for example, staples, adhesives, elastic material, or any other suitable means.

Each trigger wire 161 may include a taut portion 164 and a slack portion 165. For example, the first trigger wire 161a may include a taut portion 164a and a slack portion 165a. Likewise, the second trigger wire 161b may include a taut portion 164b and a slack portion 165b. In other examples, the slack portion may be omitted from one or more of the trigger wires (e.g., the first trigger wire 161). In other words, one or more of the trigger wires may be held taut between the nose cone and the trigger wire release mechanism 170. In these examples, the trigger wire from which the slack portion is omitted may not be engaged by the restraining member 166. The taut portion 164 of each trigger wire 161 may extend distally from the proximal end 162 of the trigger wire to the intermediate portion coupled to the handle 150. For example, the taut portion 164 of each trigger wire may extend distally from the nose cone 120 to the restraining member 166 as shown in FIGS. 2 and 4. The taut portion 164 of each trigger wire 161 may be pulled taut or maintained in tension between the nose cone 120 and the restraining member 166 to retain at least a portion of the stent graft 300 in the compressed configuration. For example, the taut portions 164a, 164b of the first and second trigger wires 161a, 161b may engage the proximal end 306 of the stent graft 300 as described above. The tension on the taut portions 164a, 164b of the first and second trigger wires 161a, 161b may prevent the proximal end 306 of the stent graft 300 from expanding. In other words, the taut portions 164 of the trigger wires 161 may resist the outward radial expansion force of the stent 305 to retain the proximal end 306 of the stent graft 300 in close proximity to the inner cannula 110.

The slack portion 165 of each trigger wire 161 may extend distally from the taut portion 164. The intermediate portion of each trigger wire 161 coupled to the handle 150 may isolate the taut portion 164 from the slack portion 165. In other words, coupling the intermediate portion of each trigger wire 161 to the handle 150 may prevent the tension on the taut portion 164 from being transmitted to the slack portion 165. For example, the slack portion 165 of each trigger wire 161 may extend between the restraining member 166 and the trigger wire release mechanism 170 as shown in FIG. 4. In this manner, a length of the slack portion 165 of each trigger wire 161 may be adjusted as further described below while maintaining tension on the taut portion 164 of the trigger wire to retain a portion of the stent graft 300 in the compressed configuration.

Figure 5:
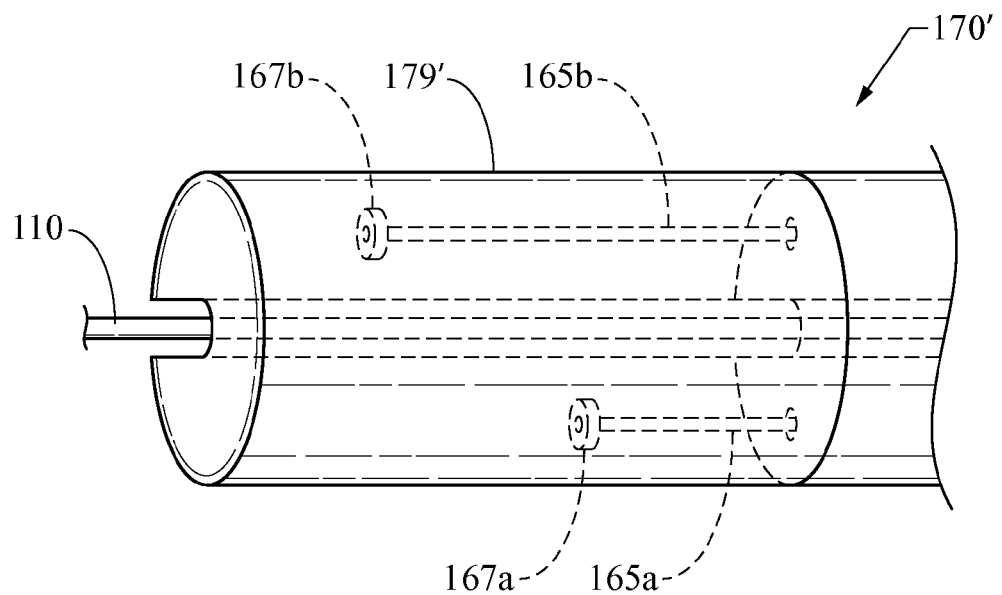
FIG. 5 depicts one example of a trigger wire release mechanism.

FIG. 5 illustrates an alternative embodiment of a trigger wire release mechanism 170'. In this embodiment, the distal ends 163a, 163b of the trigger wires 161a, 161b may be unattached or free from the trigger wire release mechanism 170'. The slack portions 165a, 165b of the respective trigger wires 161a, 161b may extend through one or more substantially longitudinal openings formed in the trigger wire release mechanism 170'. The trigger wires may be slidably received within the openings formed in the trigger wire release mechanism 170'. In this manner, the trigger wires may be slidably coupled to the trigger wire release mechanism 170'. The trigger wires 161a, 161b may include catch members 167a, 167b attached to the respective distal ends 163a, 163b. The catch members may be attached to the trigger wires by any suitable means. Alternatively, the catch members may be formed integrally with the trigger wires. The catch members may be formed from any suitable material known in the art. The catch member 167a, 167b of each trigger wire 161a, 161b may have a dimension that is greater than a diameter of the corresponding opening formed in the trigger wire release mechanism 170'. In this manner, the catch member may be incapable of passing through the corresponding opening formed in the trigger wire release mechanism. Upon retraction of the trigger wire release mechanism 170', as further described below, the trigger wire release mechanism may engage the catch members sequentially (e.g., the catch member 167a, and then the catch member 167b) to release the trigger wires from the stent graft 300 sequentially for staged release of the stent graft.

A length of each trigger wire 161 may include a length of the taut portion 164 of the trigger wire and a length of the slack portion 165 of the trigger wire. In one example, the first and second trigger wires 161a, 161b may have substantially equal lengths. The proximal end 306 of the stent graft 300 may be released (i.e., allowed to expand from the compressed configuration) by releasing the first and second trigger wires 161a, 161b therefrom. The first and second trigger wires 161a, 161b may be released from the stent graft 300 by actuation of the trigger wire release mechanism 170. For example, the trigger wire release mechanism 170 may be retracted distally relative to the handle and/or the inner cannula 110. Such movement may cause the first and second trigger wires 161a, 161b to be pulled distally and the proximal ends 162a, 162b of the first and second trigger wires to be released from the nose cone 120. Because the first and second trigger wires 161a, 161b may have substantially equal lengths, the first and second trigger wires may be released from the nose cone 120 approximately simultaneously. Such simultaneous release may enable the proximal end 306 of the stent graft 300 to expand along substantially an entire circumference thereof.

Different trigger wires may have different lengths to enable staged release (e.g., circumferentially staged release and/or longitudinally staged release) of the stent graft as further described below. In one example, the second trigger wire 161b may have a greater length than the first trigger wire 161a as shown in FIG. 4. In this example, the taut portions 164a, 164b of the first and second trigger wires 161a, 161b may have substantially equal lengths while the slack portion 165b of the second trigger wire 161b may have a greater length than the slack portion 165a of the first trigger wire 161a.

Upon initial retraction of the trigger wire release mechanism 170 a first longitudinal distance, the slack portion 165a of the first trigger wire 161a may be pulled tight between the restraining member 166 and the trigger wire release mechanism. Because the slack portion 165b of the second trigger wire 161b may have a greater length than the slack portion 165a of the first trigger wire 161a, the slack portion 165b of the second trigger wire may remain slack or loose between the restraining member 166 and the trigger wire release mechanism 170. Upon further retraction of the trigger wire release mechanism 170 a second longitudinal distance, the first trigger wire 161a may be released from the nose cone 120 while the second trigger wire may remain attached to the nose cone 120 and engaged with the stent graft 300. Releasing the first trigger wire 161a from the stent graft 300 while leaving the second trigger wire 161b engaged with the stent graft may allow partial expansion of the proximal end 306 of the stent graft. In other words, the stent graft 300 may be allowed to expand from the contracted configuration along only a portion of the circumference thereof. The release of the first trigger wire 161a may be a first stage of a staged release of the proximal end 306 of the stent graft 300.

Upon even further retraction of the trigger wire release mechanism 170, the second trigger wire 161b may be released from the nose cone 120, whereby complete expansion of the proximal end 306 of the stent graft 300 may be allowed. In other words, the stent graft 300 may be allowed to expand from the contracted configuration along substantially an entire circumference thereof. The release of the second trigger wire 161b may be a second stage of the staged release of the proximal end 306 of the stent graft 300. Although operation of the introducer for staged release of the prosthesis 300 has been described above with reference to the trigger wire release mechanism 170 shown in FIG. 4, the description is equally applicable to the trigger wire release mechanism 170' shown in FIG. 5.

The trigger wire release mechanism 170 may include a spacer 179 at the proximal end thereof. The spacer 179 may be configured as a generally tubular member having a substantially cylindrical shape. When the trigger wire release mechanism 170 is in the delivery position as shown in FIG. 1, a chamber may be formed within the spacer 179 between an inner surface of the spacer and the distal portion 155 of the handle 150. Alternatively, or additionally, a spacer 179' may be disposed at the distal end of the trigger wire release mechanism, as shown in FIG. 5, to form the chamber distal to the trigger wire release mechanism. The slack portion 165 of each trigger wire 161 may be disposed within the chamber until released therefrom by, for example, retraction of the trigger wire release mechanism 170. Such a chamber also may be formed by a recessed portion in the handle 150 positioned adjacent to the trigger wire release mechanism 170 in the delivery position. The chamber may receive the slack portion 165 of each trigger wire 161 to conceal the slack portion from view and/or to prevent entanglement of the slack portion with the physician's hands or other tools or instruments. In other words, the slack portions extending distally from the taut portions of the trigger wires may be positioned within the chamber. With the trigger wire release mechanism 170 in the delivery position, the slack portions of the trigger wires may be folded, bunched, or otherwise gathered within the chamber. The chamber may prevent premature or unintentional release of a trigger wire which may be caused by, for example, snagging the slack portion while positioning the introducer.

Although the foregoing description has referred to a trigger wire system having two trigger wires, the description is equally applicable to a trigger wire system having any number of trigger wires. Accordingly, it will be apparent to one of ordinary skill in the art that any number of trigger wires may be used to allow expansion of the proximal end of a prosthesis in any number of stages. The description also is equally applicable to a trigger wire system engaging any portion of a prosthesis, such as a distal end or an intermediate portion thereof. Such modifications are contemplated by and within the scope of this disclosure.

Staged release, or selective expansion of only a portion of the proximal end 306 of the stent graft 300 may be beneficial. For example, a trigger wire removal force (i.e., the force required to pull the trigger wire release mechanism) may be high, especially for an introducer having a greater number (such as 5, 6, or more) of trigger wires, when all of the trigger wires are pulled from the nose cone simultaneously. Staggering or staging the release of the trigger wires as described above may reduce the force required to pull the trigger wire release mechanism by allowing fewer than all of the trigger wires to be released from the nose cone simultaneously. Each trigger wire may be released from the nose cone individually as described above. Alternatively, groups of trigger wires, such as pairs of trigger wires, may be released simultaneously as further described below. Reducing the force required to pull the trigger wire release mechanism may provide a physician with a desirable positive feedback and smooth, continuous tactile experience during deployment of a prosthesis.

Figure 6:
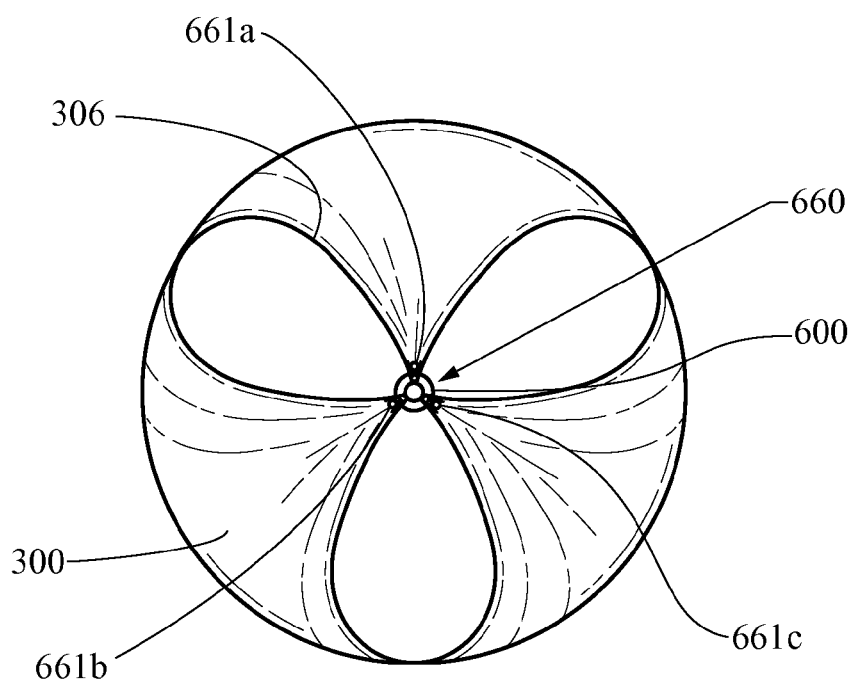
FIGS. 6-7 illustrate a method of deploying a stent graft in stages.
Figure 7:
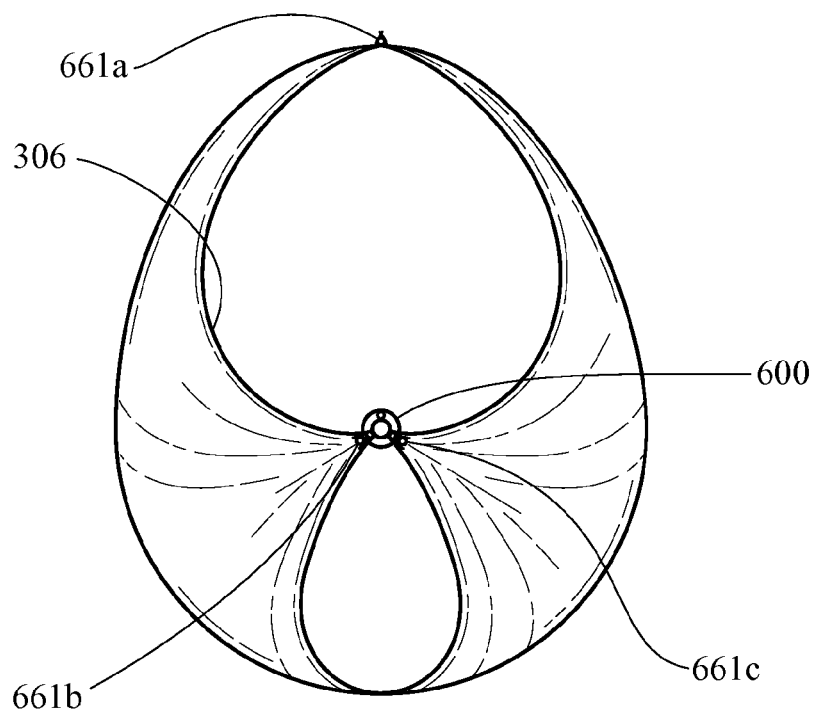

A trigger wire system having multiple trigger wires may be employed to enable staged or staggered release of a portion of a prosthesis. For example, FIGS. 6-7 depict transverse cross sectional views taken along the proximal end of the stent graft 300 loaded on another example of an introducer 600. The introducer 600 may include a trigger wire system having first, second, and third trigger wires 661a, 661b, 661c. Each trigger wire 661 may have a taut portion and a slack portion as described above with reference to the trigger wire system 160. The taut portions of the first, second, and third trigger wires 661a, 661b, 661c may have substantially equal lengths. The slack portions of the second and third trigger wires 661b, 661c may have greater lengths than the slack portion of the first trigger wire 661a. The slack portions of the second and third trigger wires 661b, 661c also may have substantially equal lengths. The trigger wires 661 may be engaged with the proximal end 306 of the stent graft 300 as shown in FIG. 6. Upon retraction of the trigger wire release mechanism, the first trigger wire 661a with the shortest slack portion may disengage the proximal end 306 of the stent graft 300 while the second and third trigger wires remain engaged with the proximal end of the stent graft. Such selective disengagement of the first trigger wire 661a may enable partial expansion of the proximal end 306 of the stent graft 300 as shown in FIG. 7. Such partial expansion may be expansion of a circumferential portion of the stent graft 300. With the stent graft 300 in such a partially expanded configuration, a physician may be able to reposition the stent graft within a body vessel prior to complete expansion of the stent graft. The physician may be able to reposition the partially expanded stent graft because the proximal end thereof has not fully expanded to engage the wall of the body vessel. Upon further retraction of the trigger wire release mechanism, the second and third trigger wires 661b, 661c with equal length slack portions may disengage the proximal end 306 of the stent graft 300 substantially simultaneously to allow complete expansion thereof. In this manner, the expansion of the proximal end 306 of the stent graft 300 may be circumferentially staged. The proximal end 306 of the stent graft 300 may engage the wall of the body vessel upon complete expansion thereof to fix the position of the stent graft relative to the body vessel.

Figure 8:
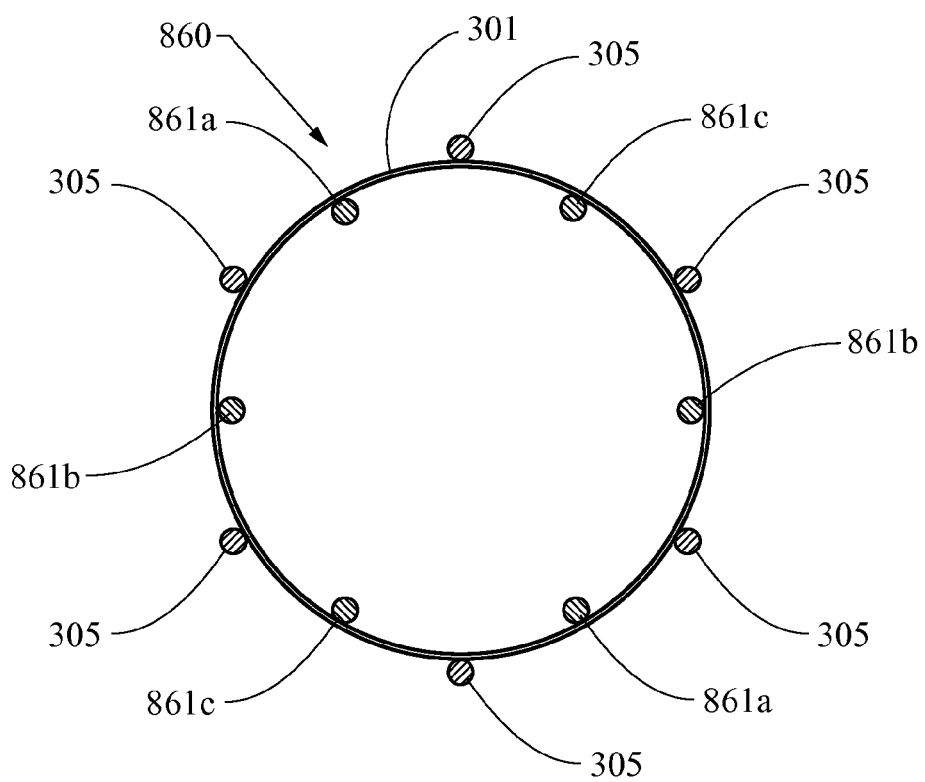
FIG. 8 depicts one example of a trigger wire system for staged deployment of a stent graft.

FIG. 8 depicts a transverse cross sectional view taken along an engaged portion (such as the proximal end) of the stent graft 300 engaged by another example of a trigger wire system. Each trigger wire 861 may engage the stent 305 to retain the proximal end of the stent graft 300 in the compressed configuration. The trigger wire system 860 may include six trigger wires. Each trigger wire may have a taut portion and a slack portion as described above with reference to the trigger wire system 160. The six trigger wires may be grouped into first, second, and third pairs of trigger wires 861a, 861b, 861c. Such a grouping may allow for a three-stage release of the proximal end of the stent graft 300 as further described below. Taut portions of the individual trigger wires of each pair of trigger wires may have substantially equal lengths, and slack portions of the individual trigger wires of each pair of trigger wires may have substantially equal lengths. The taut portions of the first, second, and third pairs of trigger wires 861a, 861b, 861c may have substantially equal lengths. The slack portions of the second and third pairs of trigger wires 861b, 861c may have greater lengths than the slack portions of the first pair of trigger wires 861a. The slack portions of the third pair of trigger wires 861c may have greater lengths than the slack portions of the second pair of trigger wires 861c. In other words, the first pair of trigger wires 861a may have shorter slack portions than the second pair of trigger wires 861b, and the second pair of trigger wires may have shorter slack portions than the third pair of trigger wires 861c.

The trigger wires may be engaged with the proximal end 306 of the stent graft 300 as described above with reference to FIG. 2. The trigger wires may be disposed circumferentially about the stent graft 300 as shown in FIG. 8. For example, the trigger wires may be spaced from one another circumferentially about the stent 305 to engage the stent at different circumferential positions (e.g., at different bent segments or apices of the stent). Upon retraction of the trigger wire release mechanism, the first pair of trigger wires 861a with the shortest slack portions may disengage the proximal end 306 of the stent graft 300 substantially simultaneously while the second and third pairs of trigger wires 861b, 861c remain engaged with the proximal end of the stent graft. The release of the first pair of trigger wires 861a may be a first stage of the staged release of the proximal end 306 of the stent graft 300. Upon further retraction of the trigger wire release mechanism, the second pair of trigger wires 861b may disengage the proximal end 306 of the stent graft 300 substantially simultaneously while the third pair of trigger wires 861c remain engaged with the proximal end of the stent graft. The release of the second pair of trigger wires 861b may be a second stage of the staged release of the proximal end 306 of the stent graft 300. Upon still further retraction of the trigger wire release mechanism, the third pair of trigger wires 861c may disengage the proximal end 306 of the stent graft 300 substantially simultaneously to allow complete expansion thereof. The release of the third pair of trigger wires 861c may be a third stage of the staged release of the proximal end 306 of the stent graft 300. The proximal end 306 of the stent graft 300 may engage the wall of the body vessel upon complete expansion thereof to fix the position of the stent graft relative to the body vessel.

In the example of FIG. 8, the individual trigger wires of each pair of trigger wires may be positioned opposite one another relative to the circumference of the stent graft 300. In other words, each pair of trigger wires may include two diametrically positioned trigger wires as shown in FIG. 8. In this manner, the proximal end 306 of the stent graft 300 may be released in a symmetrical manner at each stage of release. Alternatively, the trigger wires may be positioned in any pattern around the circumference of the stent graft 300 to release the proximal end 306 thereof in any desirable manner.

Releasing the proximal end of the stent graft in stages may reduce the force required to pull the trigger wire release mechanism as described above. For example, a physician deploying the stent graft using the trigger wire system of FIG. 8 would feel the force of only two wires at each stage of release as opposed to all six wires at the same time during a single stage of release. Staged release also may have the additional advantage of allowing precise placement of the proximal end of the stent graft within the body vessel. For example, staged deployment may prevent the proximal end of the stent graft from springing open rapidly (such as may occur upon simultaneous release of all of the trigger wires) to provide for a more controlled, gradual expansion of the stent graft. This may prevent the position of the proximal end of the stent graft relative to the body vessel from changing during expansion of the proximal end of the stent graft. Also for example, staged deployment may enable the stent graft to be repositioned within the body vessel between stages. In other words, the stent graft may be repositioned prior to complete expansion of the stent graft which may fix the stent graft in place along the vessel wall. Additionally, providing trigger wires having slack portions of different lengths may enable such staged deployment without requiring multiple trigger wire release mechanisms. In other words, providing trigger wires having slack portions of different lengths may enable a portion of the stent graft to be released in stages using a single trigger wire release mechanism. Such a configuration may simplify operation of the introducer by requiring a single pulling action to release a portion of the stent graft in multiple stages.

The lengths of the slack portions of different trigger wires may be adjustable to achieve a prescribed release of a portion of the stent graft. For example, it may be desirable to release the proximal end of the stent graft asymmetrically to place the proximal end of the stent graft within a curved body vessel. In such a situation, it may be desirable to release a first portion of the circumference of the proximal end of the stent graft positioned on an outer radius of the curve before releasing a second portion of the circumference positioned on an inner radius of the curve. In preparing for such a procedure, a physician may adjust the lengths of the slack portions of the trigger wires so that the trigger wires engaging the first portion of the proximal end of the stent graft may have a shorter length than the slack portions of the trigger wires engaging the second portion. The physician may adjust the length of the slack portion of a trigger wire by, for example, sliding the trigger wire proximally or distally through the opening 178 in the trigger wire release mechanism 170 or sliding the catch member proximally or distally along the trigger wire. Upon retraction of the trigger wire release mechanism, the trigger wires having shorter slack portions may be released first, allowing the first portion of the proximal end of the stent graft to expand to engage the body vessel along the outer radius of the curve. Upon further retraction of the trigger wire release mechanism, the trigger wires having longer slack portions may be released, allowing complete expansion of the proximal end of the stent graft.

A trigger wire system as described above may be used for staged deployment of different portions of a prosthesis. For example, a trigger wire system may include two trigger wires. The first trigger wire may engage the proximal end of the stent graft to retain the proximal end in the compressed configuration. The second trigger wire may engage the distal end of the stent graft to retain the distal end in the compressed configuration. In such an arrangement, the taut portion of the first trigger wire may have a longer length than the taut portion of the second trigger wire. This longer length may correspond to a portion of the taut portion of the first trigger wire extending within the lumen of the stent graft from the distal end to the proximal end thereof. Also, the slack portion of the first trigger wire may have a shorter length than the slack portion of the second trigger wire. Upon retraction of the trigger wire release mechanism, the first trigger wire with the shorter slack portion may be released from the proximal end of the stent graft to allow expansion thereof. Because the second trigger wire may have a longer slack portion, the second trigger wire may remain engaged with the distal end of the stent graft to retain the distal end in the compressed configuration. Upon further retraction of the trigger wire release mechanism, the second trigger wire may be released from the distal end of the stent graft to allow expansion thereof. In this manner, staged expansion of the proximal and distal ends of the stent graft may be accomplished by retracting a single trigger wire release mechanism.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

I claim:

1. A prosthesis introducer system comprising:
    an introducer comprising a proximal end, a distal end, at least one trigger wire lumen extending at least partly between the proximal end and the distal end, a trigger wire release mechanism positioned near the distal end of the introducer, and a restraining member positioned near the distal end of the introducer; and
    a first trigger wire and a second trigger wire extending through the at least one trigger wire lumen, each of the first trigger wire and the second trigger wire comprising a proximal portion releasably coupleable to a portion of a prosthesis and a distal portion coupled to the trigger wire release mechanism, at least the second trigger wire being engaged by the restraining member;
    wherein each of the first trigger wire and the second trigger wire comprises a taut portion, and at least the second trigger wire comprises a slack portion extending distally from the taut portion and positioned distal of the restraining member; and
    wherein, upon actuation of the trigger wire release mechanism, the first trigger wire is releasable from the prosthesis and then the second trigger wire is releasable from the prosthesis subsequent to the release of the first trigger wire.

2. The prosthesis introducer system of claim 1, wherein the introducer further comprises an inner cannula and an outer cannula, the inner cannula extends longitudinally within a lumen of the outer cannula, and the at least one trigger wire lumen comprises an annular space between the inner cannula and the outer cannula.

3. The prosthesis introducer system of claim 2, wherein the introducer further comprises a sheath, and the inner cannula and the outer cannula extend longitudinally within a lumen of the sheath.

4. The prosthesis introducer system of claim 1, wherein the introducer further comprises a handle attached to the distal end of the introducer, and the trigger wire release mechanism is removably coupled to the handle.

5. The prosthesis introducer system of claim 4, wherein the introducer further comprises a chamber between the trigger wire release mechanism and the handle, and the slack portion of at least the second trigger wire is received within the chamber.

6. The prosthesis introducer system of claim 4, wherein the restraining member comprises a ring member at least partially circumscribing the handle, and at least the second trigger wire is received radially between the restraining member and the handle.

7. A prosthesis introducer system comprising:
    an introducer comprising a proximal end, a distal end, at least one trigger wire lumen extending at least partly between the proximal end and the distal end, a trigger wire release mechanism positioned near the distal end of the introducer, and a restraining member positioned near the distal end of the introducer; and
    a first trigger wire and a second trigger wire extending through the at least one trigger wire lumen, each of the first trigger wire and the second trigger wire comprising a proximal portion releasably coupleable to a portion of a prosthesis and a distal portion coupled to the trigger wire release mechanism, at least the second trigger wire being engaged by the restraining member;
    wherein each of the first trigger wire and the second trigger wire comprises a taut portion, and at least the second trigger wire comprises a slack portion extending distally from the taut portion and positioned distal of the restraining member; and
    a third trigger wire and a fourth trigger wire, each of the third trigger wire and the fourth trigger wire comprising a proximal portion releasably coupleable to the portion of the prosthesis and a distal portion coupled to the trigger wire release mechanism, at least the fourth trigger wire being engaged by the restraining member;
    wherein each of the third trigger wire and the fourth trigger wire comprises a taut portion, at least the fourth trigger wire comprises a slack portion extending distally from the taut portion and positioned distal of the restraining member, and the taut portions of the first trigger wire, the second trigger wire, the third trigger wire, and the fourth trigger wire have substantially equal lengths
    wherein, upon actuation of the trigger wire release mechanism, the first trigger wire is releasable from the prosthesis and then the second trigger wire is releasable from the prosthesis subsequent to the release of the first trigger wire.

8. The prosthesis introducer system of claim 7, wherein each of the first trigger wire and the third trigger wire is engaged by the restraining member and comprises a slack portion extending distally from the taught portion and positioned distal of the restraining member, the slack portions of the first trigger wire and the third trigger wire have substantially equal lengths, the slack portions of the second trigger wire and the fourth trigger wire have substantially equal lengths, and the slack portions of the second trigger wire and the fourth trigger wire are longer than the slack portions of the first trigger wire and the third trigger wire, and
    wherein, upon actuation of the trigger wire release mechanism, the first trigger wire and the third trigger wire are releasable from the prosthesis and then the second trigger wire and the fourth trigger wire are releasable from the prosthesis subsequent to the release of the first trigger wire and the third trigger wire.

9. The prosthesis introducer system of claim 8, wherein the first trigger wire and the third trigger wire are coupleable to the prosthesis at a first pair of diametrically opposing points with respect to a circumference of the prosthesis and the second trigger wire and the fourth trigger wire are coupleable to the prosthesis at a second pair of diametrically opposing points with respect to the circumference of the prosthesis.

10. The prosthesis introducer system of claim 7, wherein the third trigger wire is engaged by the restraining member and comprises a slack portion extending distally from the taught portion and positioned distal of the restraining member, the slack portion of the third trigger wire is longer than the slack portion of the second trigger wire, and the slack portion of the fourth trigger wire is longer than the slack portion of the third trigger wire, and, upon actuation of the trigger wire release mechanism, the third trigger wire is releasable from the prosthesis subsequent to the release of the second trigger wire, and the fourth trigger wire is releasable from the prosthesis subsequent to the release of the third trigger wire.

11. A prosthesis introducer system comprising:
an introducer comprising an inner cannula and an outer cannula, the inner cannula comprising a proximal end, a distal end, and a lumen extending between the proximal end and the distal end thereof, the outer cannula comprising a proximal end, a distal end, and a lumen extending between the proximal end and the distal end thereof, the inner cannula being at least partially received within the lumen of the outer cannula, the introducer further comprising a trigger wire release mechanism positioned near the distal end of the outer cannula and a restraining member positioned near the distal end of the outer cannula;
an expandable endoluminal prosthesis positioned on the inner cannula; and
a first trigger wire and a second trigger wire extending through an annular space between the inner cannula and the outer cannula, each of the first trigger wire and the second trigger wire comprising a proximal portion releasably coupled to the prosthesis and a distal portion coupled to the trigger wire release mechanism, each of the first trigger wire and the second trigger wire being engaged by the restraining member;
wherein each of the first trigger wire and the second trigger wire comprises a taut portion and a slack portion extending distally from the taut portion and positioned distal of the restraining member, and the slack portion of the second trigger wire is longer than the slack portion of the first trigger wire; and
wherein, upon actuation of the trigger wire release mechanism, the first trigger wire is released from the prosthesis and then the second trigger wire is released from the prosthesis subsequent to the release of the first trigger wire.

12. The prosthesis introducer system of claim 11, wherein the first trigger wire is releasably coupled to a proximal portion of the prosthesis to retain the proximal portion of the prosthesis in a compressed configuration, and the second trigger wire is releasably coupled to a distal portion of the prosthesis to retain the distal portion of the prosthesis in a compressed configuration.

13. The prosthesis introducer system of claim 12, wherein the taut portion of the first trigger wire is longer than the taut portion of the second trigger wire.

14. The prosthesis introducer system of claim 11, wherein each of the first trigger wire and the second trigger wire is releasably coupled to a proximal portion of the prosthesis.

15. The prosthesis introducer system of claim 14, wherein, upon actuation of the trigger wire release mechanism, the proximal portion of the prosthesis expands asymmetrically from a compressed configuration.

16. The prosthesis introducer system of claim 11, further comprising a first pair of trigger wires and a second pair of trigger wires, the first pair of trigger wires comprising the first trigger wire and a third trigger wire, the second pair of trigger wires comprising the second trigger wire and a fourth trigger wire, each of the third trigger wire and the fourth trigger wire comprising a proximal portion releasably coupled to the prosthesis and a distal portion coupled to the trigger wire release mechanism, each of the third trigger wire and the fourth trigger wire being engaged by the restraining member and comprising a taut portion and a slack portion extending distally from the taut portion and positioned distal of the restraining member;
wherein the taut portions of the first pair of trigger wires and the second pair of trigger wires have substantially equal lengths and the slack portions of the second pair of trigger wires are longer than the slack portions of the first pair of trigger wires, and
wherein, upon actuation of the trigger wire release mechanism, the first pair of trigger wires is released from the prosthesis and then the second pair of trigger wires is released from the prosthesis subsequent to the first pair of trigger wires.

17. The prosthesis introducer system of claim 16, wherein, the proximal portions of the first pair of trigger wires and the second pair of trigger wires are releasably coupled to a proximal portion of the prosthesis, and, upon actuation of the trigger wire release mechanism, the proximal portion of the prosthesis expands symmetrically from a compressed configuration.

* * * * *